US012601008B2

(12) United States Patent　　　　　　　　(10) Patent No.:　US 12,601,008 B2
Lemmon　　　　　　　　　　　　　　　　　(45) Date of Patent:　　Apr. 14, 2026

(54) USING HAIRPIN FORMATION TO IDENTIFY DNA AND RNA SEQUENCES HAVING A TARGET NUCLEIC ACID SEQUENCE

(71) Applicant: Florida State University Research Foundation, Inc., Tallahassee, FL (US)

(72) Inventor: Alan R. Lemmon, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 703 days.

(21) Appl. No.: 17/980,960

(22) Filed: Nov. 4, 2022

(65) Prior Publication Data

US 2023/0348962 A1　　Nov. 2, 2023

Related U.S. Application Data

(60) Provisional application No. 63/275,619, filed on Nov. 4, 2021.

(51) Int. Cl.
*C12Q 1/68*　　　　(2018.01)
*C12Q 1/6855*　　　(2018.01)

(52) U.S. Cl.
CPC ................................. *C12Q 1/6855* (2013.01)

(58) Field of Classification Search
None
See application file for complete search history.

(56) References Cited

U.S. PATENT DOCUMENTS

| | | |
|---|---|---|
| 5,215,899 A | 6/1993 | Dattagupta |
| 5,955,276 A | 9/1999 | Morgante et al. |
| 2002/0012924 A1 | 1/2002 | Schumm et al. |
| 2003/0003205 A1 | 1/2003 | Costello |
| 2005/0176023 A1 | 8/2005 | Ramon et al. |
| 2009/0203085 A1 | 8/2009 | Kurn et al. |
| 2014/0163900 A1 | 6/2014 | Erlich et al. |
| 2019/0300942 A1 * | 10/2019 | Marziali .............. C12Q 1/6869 |
| 2021/0002717 A1 | 1/2021 | Dong et al. |
| 2021/0130815 A1 | 5/2021 | Lemmon |
| 2021/0207213 A1 | 7/2021 | Eijk et al. |

OTHER PUBLICATIONS

International Search Report of Apr. 13, 2023 for PCT/US2022/048985.
International Search Report of Apr. 9, 2021 for PCT/US2020/059168.

* cited by examiner

*Primary Examiner* — Aaron A Priest
(74) *Attorney, Agent, or Firm* — GrayRobinson, P.A.

(57)　　　　　　ABSTRACT

DNA or RNA including a target nucleotide sequence are amplified by placing a probe nucleotide sequence on the DNA or RNA. The probe nucleotide sequence is complementary to the target nucleotide sequence. The interaction between the probe nucleotide sequence and target nucleotide sequence causes the single-stranded DNA to form a hairpin. The hairpinned single-stranded DNA are selected for amplification.

7 Claims, 5 Drawing Sheets

Specification includes a Sequence Listing.

Cool

Hairpin does not form if target absent

Hairpin forms when fragment contains target region

USING HAIRPIN FORMATION TO IDENTIFY DNA AND RNA SEQUENCES HAVING A TARGET NUCLEIC ACID SEQUENCE

CROSS-REFERENCE TO RELATED APPLICATION

This claims the benefit of priority to U.S. provisional Application No. 63/275,619, filed Nov. 4, 2021, which is incorporated by reference in its entirety.

FIELD

This relates to the field of genetics and, more particularly, to evaluating genomic variation.

SEQUENCE LISTING

The application contains a Sequence Listing electronically submitted to the United States Patent and Trademark Office as an XML file named "Sequence_Listing.xml," which was created Jul. 21, 2023 and is 7,000 bytes. The information contained in the Sequence Listing is incorporated by reference herein in its entirety

BACKGROUND

Genotyping by using single nucleotide polymorphisms or single sequence repeats, such as microsatellites, currently requires substantial upfront investment to yield an efficient system. Multiplex PCR utilizes several pairs of primers simultaneously to enrich DNA for a set of loci using a single PCR reaction.

BRIEF SUMMARY

What is needed is a new, efficient way to identify DNA and RNA sequences having a target nucleotide sequence.

A first example method comprises amplifying a single-stranded nucleotide sequence including (a) a target region nucleotide sequence, (b) a hairpin region, and (c) a probe nucleotide sequence, the probe nucleotide sequence being complementary to the target region nucleotide sequence.

This method may include one or more of the following additional features.

Amplifying may include a polymerase chain reaction.

Amplifying may include priming the single-stranded nucleotide sequence with Common Primer A.

The single-stranded nucleotide sequence may further include Common Adapter A.

The probe nucleotide sequence may be ligated to the single-stranded nucleotide sequence by Common Adapter A.

Amplifying may include priming the single-stranded nucleotide sequence with Common Primer A and Common Primer B.

The hairpin region may be partially formed by the probe nucleotide sequence being complementary to the target region nucleotide sequence.

A second example method comprises ligating a probe nucleotide sequence to a DNA sequence or RNA sequence to form a ligated nucleotide sequence. The ligated nucleotide sequence is denatured into a single-stranded nucleotide sequence. A hairpin region is formed in the single-stranded nucleotide sequence when the single-stranded nucleotide sequence includes a target region nucleotide sequence that is complementary with the probe nucleotide sequence. The single-stranded nucleotide sequence with the formed hairpin region is amplified.

This method may include one or more of the following additional features.

Amplifying may be achieved by a polymerase chain reaction.

Amplifying may include priming the single-stranded nucleotide sequence with Common Primer A.

The single-stranded nucleotide sequence may further include Common Adapter A.

The probe nucleotide sequence may be ligated to the single-stranded nucleotide sequence by Common Adapter A.

Amplifying may include priming the single-stranded nucleotide sequence with Common Primer A and Common Primer B.

The hairpin region may be formed by the probe nucleotide sequence being complementary to the target region nucleotide sequence.

A third example method comprises ligating an adapter nucleotide sequence and a probe nucleotide sequence to a DNA sequence or RNA sequence to form a ligated nucleotide sequence. The ligated nucleotide sequence is denatured to separate the ligated nucleotide sequence into a single-stranded nucleotide sequence. The single-stranded nucleotide sequence is cooled to allow the single-stranded nucleotide sequence to form a hairpin region when the single-stranded nucleotide sequence includes a target region nucleotide sequence that is complementary with the probe nucleotide sequence. The single-stranded nucleotide sequence is digested to remove the adapter nucleotide sequence if the single-stranded nucleotide sequence does not include the target region nucleotide sequence. The single-stranded nucleotide sequence with the formed hairpin region is amplified.

This method may include one or more of the following additional features.

Amplifying may be achieved by a polymerase chain reaction.

Amplifying may include priming the single-stranded nucleotide sequence with Common Primer A.

The adapter nucleotide sequence may include Common Adapter A.

The probe nucleotide sequence may be ligated to the adapter nucleotide sequence, the adapter nucleotide sequence including Common Adapter A.

Amplifying may include priming the single-stranded nucleotide sequence with Common Primer A and Common Primer B.

The hairpin region may be formed by the probe nucleotide sequence being complementary to the target region nucleotide sequence.

An example composition comprises a single-stranded nucleotide sequence including (a) a target region nucleotide sequence, (b) a hairpin region, and (c) a probe nucleotide sequence, the probe nucleotide sequence being complementary to the target region nucleotide sequence.

This composition may include one or more of the following additional features.

The single-stranded nucleotide sequence may include Common Adapter A.

The probe nucleotide sequence may be ligated to the single-stranded nucleotide sequence by Common Adapter A.

The hairpin region may be partially formed by the probe nucleotide sequence being complementary to the target region nucleotide sequence.

These example methods and composition may include any combination of features of the aforementioned methods and composition.

DETAILED DESCRIPTION OF EXAMPLE EMBODIMENTS

This disclosure describes exemplary embodiments, but not all possible embodiments of the compositions and methods. Where a particular feature is disclosed in the context of a particular example, that feature can also be used, to the extent possible, in combination with and/or in the context of other features and examples. The compositions and methods may be embodied in many different forms and should not be construed as being limited to only the features and examples described here.

Certain examples of the compositions and methods described here may reduce the upfront investment and provide a rapid and less expensive way to obtain genotype data in any organism. It may also avoid the primary limiting factor of multiplex PCR, which is the primer dimer.

Certain examples of the compositions and methods described here are more flexible in terms of the type of genomic markers that can be evaluated, including SNP, STR (microsatellites), insertions, deletions, and longer DNA sequence variations.

The compositions and methods may be used to obtain randomly distributed (unbiased) markers, or specific genomic regions. The number of regions targeted is also flexible. This may reduce the upfront development time compared to conventional genotyping techniques. Bioinformatic analyses of existing genomes or preliminary DNA sequence data can be conducted quickly to ascertain the most appropriate probes, which are nucleotides that are complementary to DNA target regions. The methods may be conducted with little hands-on time.

An advantageous feature of certain examples of the methods includes enriching genomic DNA for downstream sequencing and genotyping.

The compositions and methods described here are based on the idea of using the formation of hairpin regions in nucleotide sequences to determine whether the nucleotide sequences being evaluated contain a pre-determined target nucleotide sequence. The formation of a hairpin region is promoted by adding a probe nucleotide sequence that is complementary to the target nucleotide sequence to the nucleotide sequence being evaluated. The hairpin region forms due to the interaction between the complementary nucleotide sequences.

A "hairpin region" is a loop that forms in a nucleotide sequence when a section of the sequence folds and forms base pairs with another section of the same sequence, which creates a loop-like region in the structure of the sequence.

Figure 1:
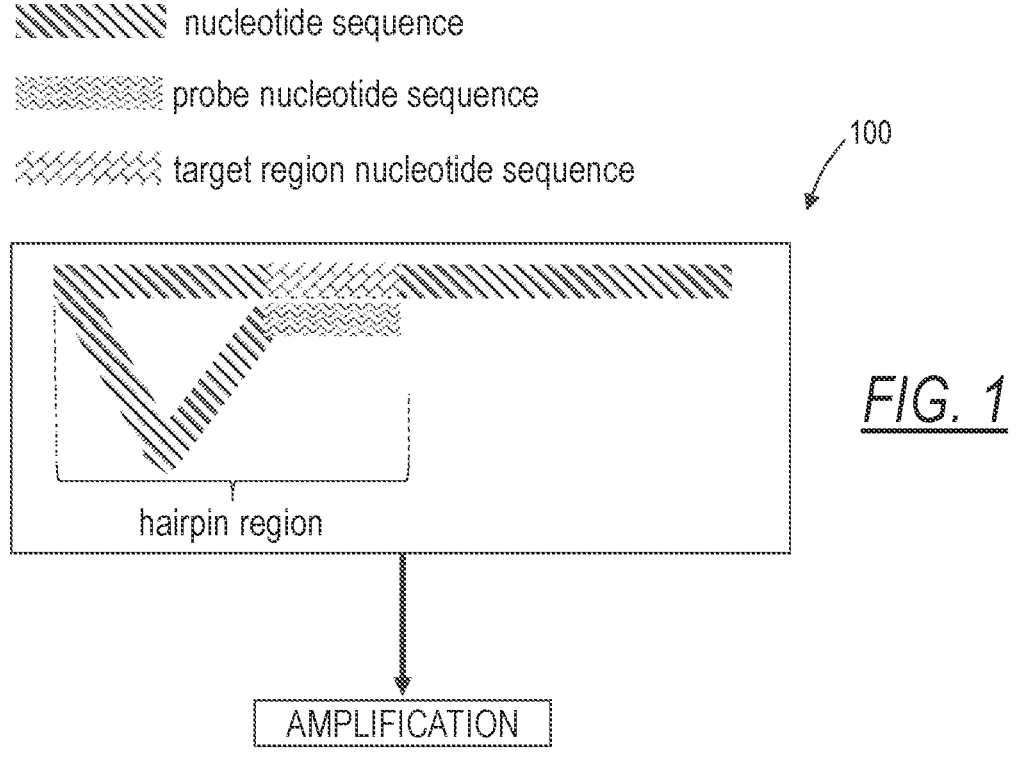
FIG. 1 is a block diagram illustrating a first example of a genotyping method.

Referring to FIG. 1, a first example of a genotyping method 100 includes amplifying a single-stranded nucleotide sequence including (a) a target region nucleotide sequence, (b) a hairpin region, and (c) a probe nucleotide sequence. The probe nucleotide sequence is complementary to the target region nucleotide sequence.

This method advantageously promotes hairpin region formation by using the probe nucleotide sequence that is complementary to the target region nucleotide sequence. If the target region nucleotide sequence is absent from the single-stranded nucleotide sequence, the hairpin region will not form. The sequences in which the hairpin region forms may be selected for amplification while the sequences absent hairpin formation may be discarded. The amplification step allows sequences with the target region nucleotide sequence to be reproduced.

Figure 2:
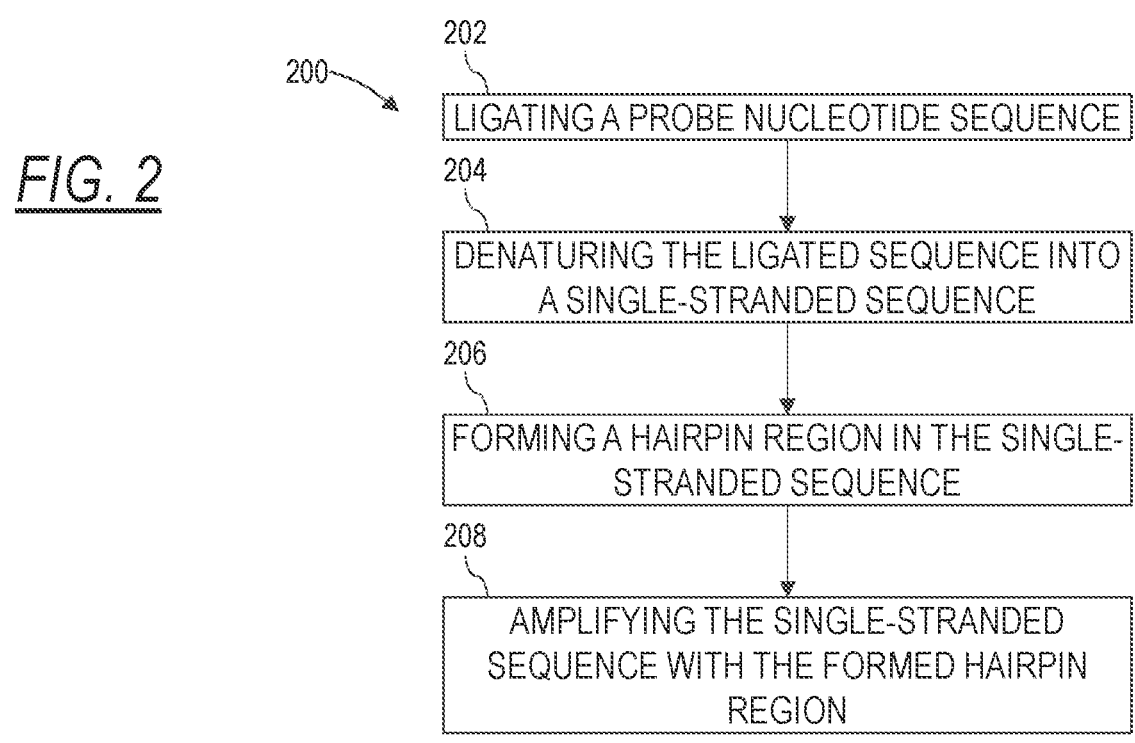
FIG. 2 is a flow chart illustrating a second example of a genotyping method.

A second example of a genotyping method 200 includes the steps outlined in FIG. 2. At block 202, a probe nucleotide sequence is ligated to a DNA sequence or RNA sequence to form a ligated sequence. At block 204, the ligated nucleotide sequence is denatured into a single-stranded nucleotide sequence. At block 206, a hairpin region is formed in the single-stranded nucleotide sequence when the single-stranded nucleotide sequence includes a target region nucleotide sequence that is complementary with the probe nucleotide sequence. At block 208, the single-stranded nucleotide sequence with the formed hairpin region is amplified.

Figure 3:
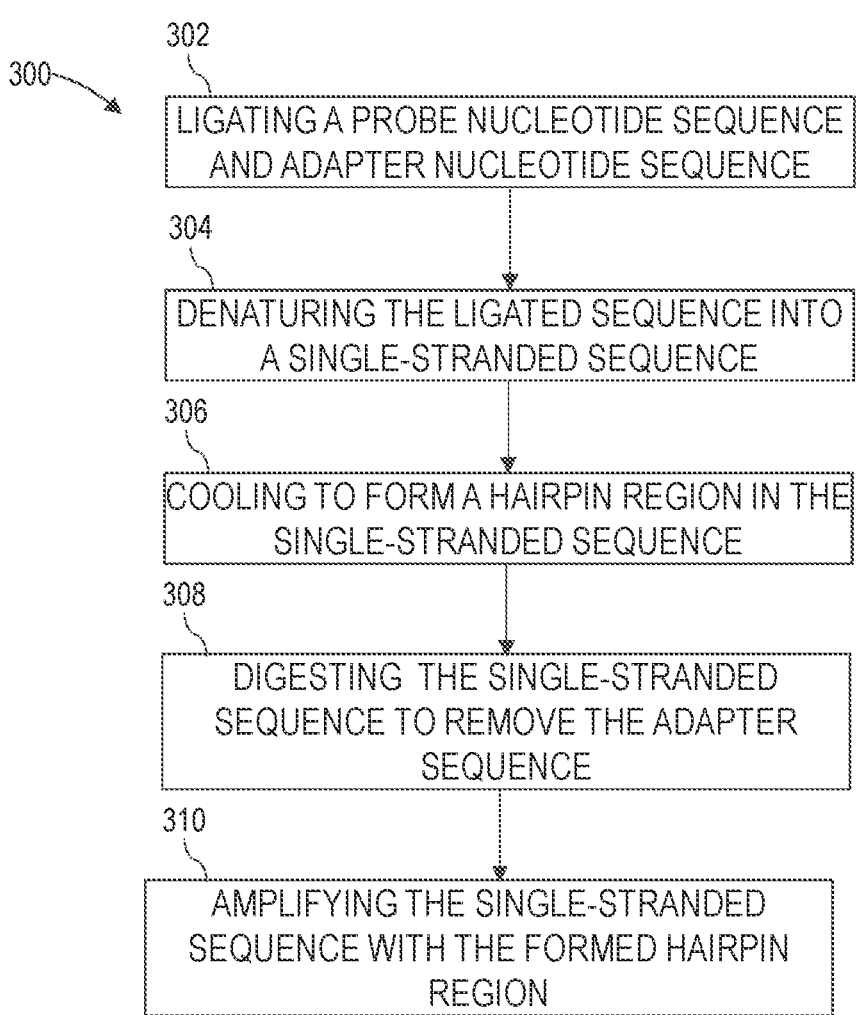
FIG. 3 is a flow chart illustrating a third example of a genotyping method.

A third example of a genotyping method 300 includes the steps outlined in FIG. 3.

At block 302 an adapter nucleotide sequence and a probe nucleotide sequence are ligated to a DNA sequence or RNA sequence to form a ligated nucleotide sequence.

At block 304, the ligated nucleotide sequence is denatured to separate the ligated nucleotide sequence into a single-stranded nucleotide sequence.

At block 306, the single-stranded nucleotide sequence is cooled to allow the single-stranded nucleotide sequence to form a hairpin region when the single-stranded nucleotide sequence includes a target region nucleotide sequence that is complementary with the probe nucleotide sequence.

At block 308, the single-stranded nucleotide sequence is digested to remove the adapter nucleotide sequence if the single-stranded nucleotide sequence does not include the target region nucleotide sequence. At block 310, the single-stranded nucleotide sequence with the formed hairpin region is amplified.

The amplifying step may include a polymerase chain reaction or "PCR" protocol. The PCR protocol may include a Phusion® Polymerase, or other polymerase, including a commercially-available thermostable polymerase.

Nucleotide sequences, such as adapters and primers may be ligated to a DNA or RNA sequence using a conventional ligation reaction. In a ligation reaction, nucleotide fragments are joined by a ligase enzyme. To help facilitate efficient ligation, the fragments mat also be annealed.

Denaturing may be achieved by a conventional DNA or RNA denaturing process, such as by melting, NaOH treatment, or salt treatment for example. Denaturing separates ligated DNA fragments.

Digestion may be achieved by a conventional DNA or RNA sequence digestion mechanism such as, for example, enzymatic digestion.

A DNA or RNA sequence may be fragmented to generate DNA/RNA fragments by enzymatic digestion of the DNA molecule. For example, fragmenting a DNA molecule with a Fragmentation Through Polymerization ("FTP") method may produce 300-600 bp dsDNA fragments. An example of a FTP method is disclosed in *Fragmentation Through Polymerization (FTP): A new method to fragment DNA for next generation sequencing*, Ignatov et al., PLoS One. 2019; 14(4): e0210374.

Generally, FTP includes the steps of (i) nicking a nucleic acid, such as DNA, with a DNAse, such as, for example, DNAse I; and (ii) performing strand displacement with a polymerase, such as, for example, SD polymerase, thereby generating blunt-ended dsDNA fragments with overlapping sequences.

Fragmenting may include sonicating the DNA molecule. Sonicating may be achieved, for example, with a commercially-available sonication system such as the Covaris® sonication system at 175 Peak Incident Power, 10% duty factor, and 200 cycles per burst for 40 seconds to produce 300-600 bp nucleic acid fragments. Other sonication conditions are possible and may be selected as desired.

Enzymatic digestion may be used instead of, or in addition to, sonication to generate DNA or RNA fragments. Other suitable fragmentation techniques may also be used.

In these methods, adapter sequences and primer sequences may be used. An adapter sequence is an oligonucleotide that can be ligated to an end of a DNA or RNA fragment. Adapter sequences may be single stranded or double stranded. A primer sequence is generally a single-stranded oligonucleotide that initiates the synthesis of DNA or RNA. Adapter sequences and primer sequences may be synthesized to have desired properties.

In these methods, the probe nucleic acid sequence, may be ligated to a DNA, RNA, or a fragment thereof by itself or as a portion of one or more adapter sequences.

The probe nucleic acid sequence is synthesized to be complementary with the target nucleotide sequence. The hairpin region is partially formed by the probe nucleotide sequence being complementary to the target region nucleotide sequence.

Adapter sequences that may be used in these methods include a first adapter sequence and a second adapter sequence. These adapter sequences are selected based on the sequencing platform. In certain examples the first adapter sequence includes Common Adapter A and the second adapter sequence includes Common Adapter B.

For downstream Illumina sequencing, the first adapter sequence may be, for example, Common Adapter A (upstream (5' from probe)) having the sequence 5'-GATCG-GAAGAGCGTCGTGTAGGGAAAGAGTGT-3' (SEQ ID NO: 1).

For downstream Illumina sequencing, the second adapter sequence may be, for example, Common Adapter B having the sequence 5'-GTGACTGGAGTTCAGACGTGTGC TCTTCCGATCT-3' (SEQ ID NO: 2).

In certain examples, the single-stranded nucleotide sequence further includes the first adapter sequence, such as Common Adapter A. The probe nucleotide sequence may be attached to the first nucleotide sequence.

In certain examples, the probe nucleotide sequence is ligated to the single-stranded nucleotide sequence by Common Adapter A.

The primer sequences are selected based on the on the sequencing platform.

For downstream Illumina sequencing the first primer sequence may be, for example, Common Primer A having the sequence 5'-AATGATACGGCGACCACCGAGATC- TACACnnnnnnnnACACTCTTTCCCTACACGAC GCTCTT-3' (SEQ ID NO: 3).

For downstream Illumina sequencing the second primer sequence may be, for example, Common Primer B having the sequence 5'-CAAGCAGAAGACGGCATACGAGAT nnnnnnnnGTGACTGGAGTTCAGACGTGT-3' (SEQ ID NO: 4).

In these primer sequences, the stretches of n's represent 8 bp nucleotide indexes (barcodes) that can vary by sample. This is standard practice for multiplexed Illumina sequencing. The indexes can be different between the two primers, representing a plate index and a well index, for example.

Other adapters and/or primers may be used in the methods, depending on the desired function.

In certain examples, the amplifying step includes priming the single-stranded nucleotide sequence with a first primer sequence such as Common Primer A.

In certain examples, the amplifying step includes priming the single-stranded nucleotide sequence with a first primer sequence, such as Common Primer A, and a second primer sequence, such as Common Primer B.

The environmental conditions for performing the steps in these methods may be selected by the user based on knowledge of the conventional conditions for annealing, denaturing, digesting, cooling, and amplifying apart from these methods.

In the PCR protocol for amplification, the annealing temperature depends on the length and composition of the primers and the identity of the polymerase. In most cases, the annealing temperature for PCR is about 5 degrees C. below the melting temperature of the primers. A skilled person can often calculate the annealing temperate by specifying the polymerase and primer sequence.

Figure 4:
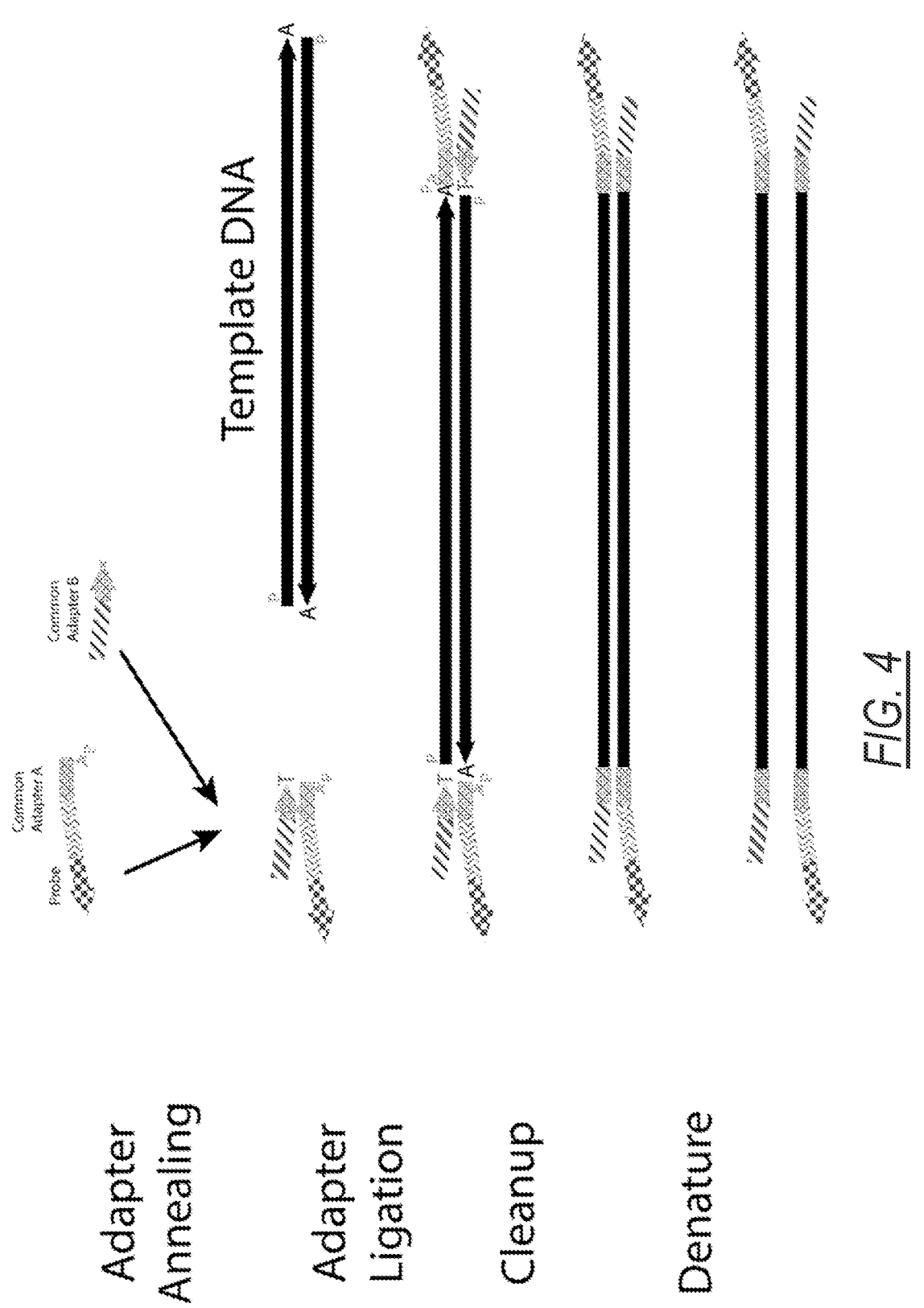
FIG. 4 is a diagram of a first part of a fourth example of a genotyping method.
Figure 5:
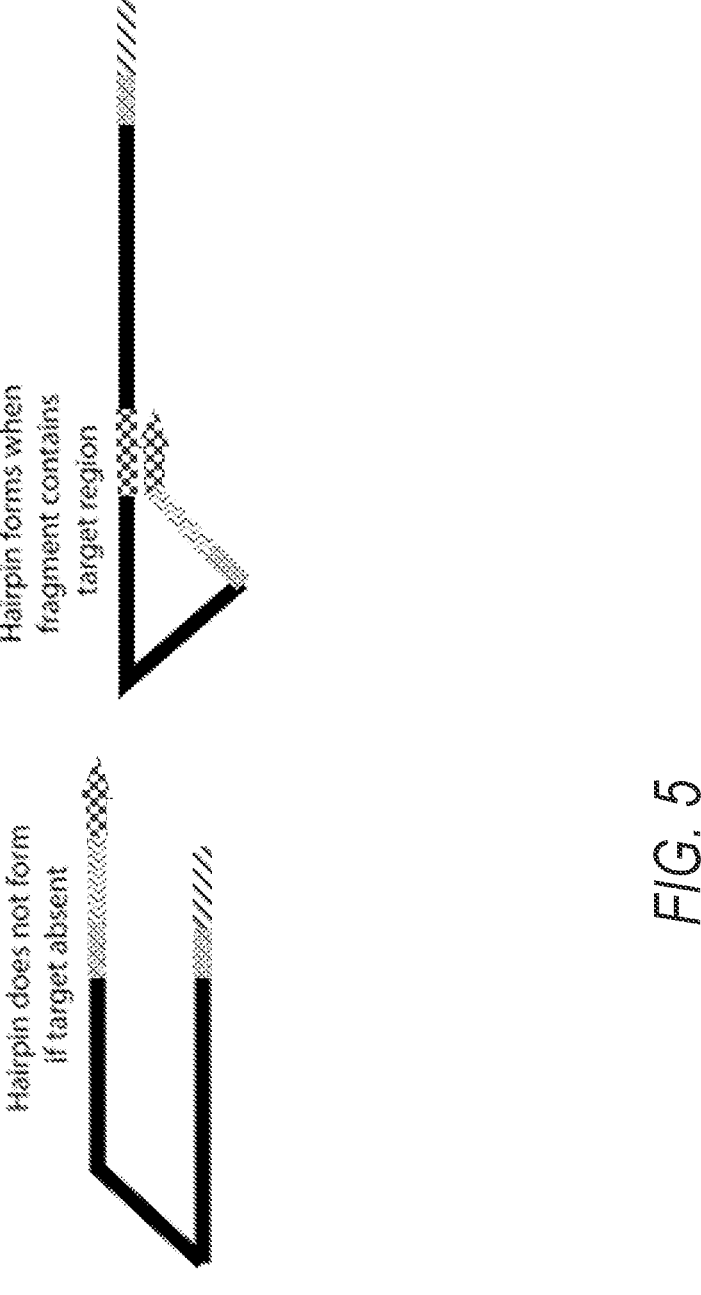
FIG. 5 is a diagram of a second part of the fourth example of a genotyping method.
Figure 6:
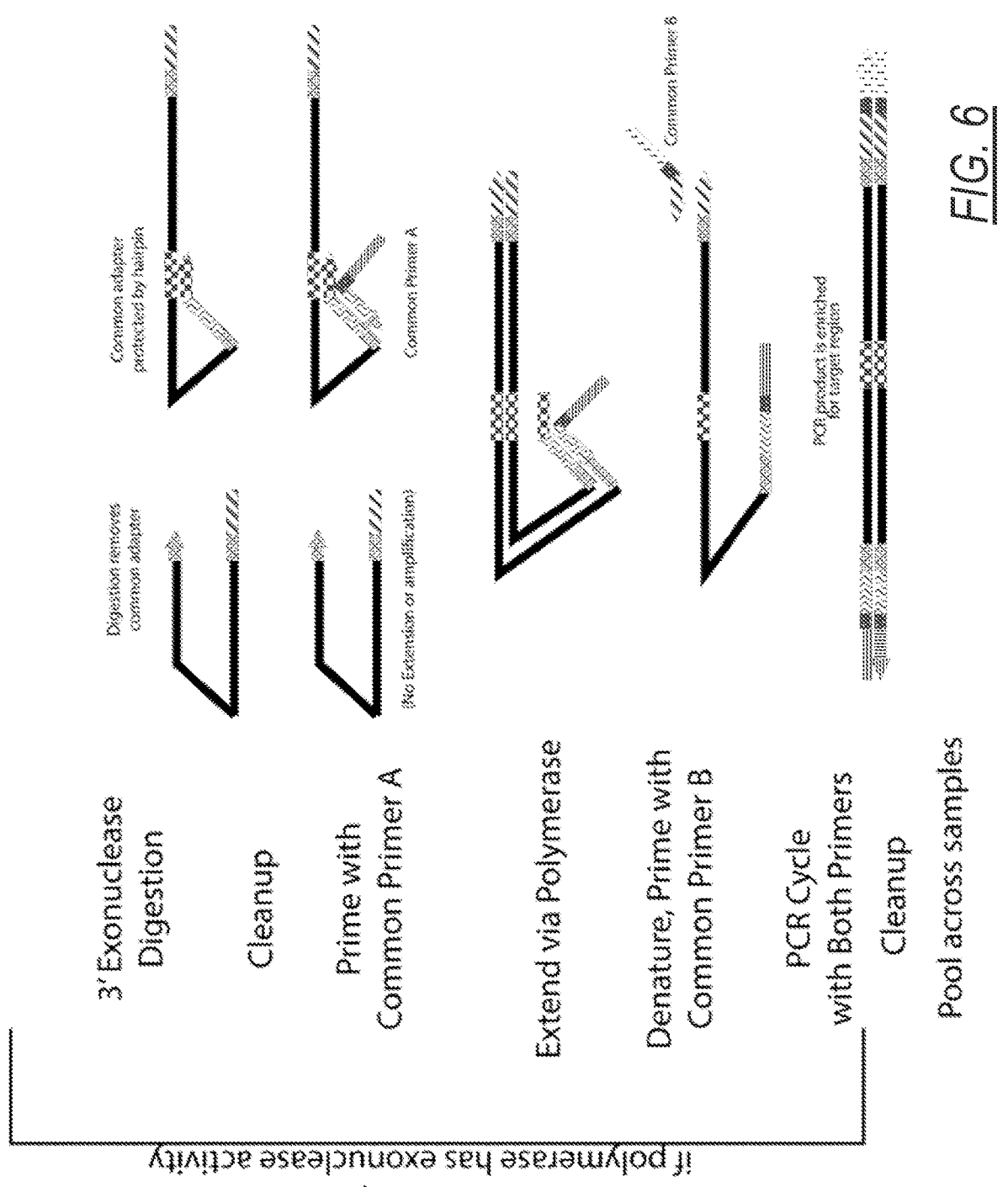
FIG. 6 is a diagram of a third part of the fourth example of a genotyping method.

Additional possible details of the aforementioned methods are now described by referring to FIGS. 4-6.

Referring to FIG. 4, an example of how a probe nucleic acid and an adapter nucleic acid sequence may be ligated to a DNA sequence or RNA sequence is now discussed. In this example, a template DNA fragment, for example, is ligated with a first adapter sequence carrying the probe nucleotide sequence and a second adapter sequence by annealing.

The template DNA fragment ligated with the first adapter sequence, probe sequence, and second adapter sequence is cleaned up and denatured. Denaturing may be achieved by a conventional DNA or RNA denaturing process. Denaturing separates the ligated DNA fragments.

The ligating step may include ligating the first adaptor sequence to at least one of the 5' and 3' ends of the DNA. The first adaptor sequence may include, for example, a common adapter such as those disclosed in Illumina Sequencing Library Preparation for Highly Multiplexed Target Capture and Sequencing, Meyer and Kircher, Cold Spring Harb Protocols; 2010; doi:10.1101/pdb.prot5448. The first adapter may be Common Adaptor A.

Referring to FIG. 5, the denatured, ligated DNA fragments are cooled to permit hairpin formation. As shown on the right, if a ligated DNA fragment includes the target region nucleotide sequence that is complementary to the probe nucleotide sequence, the DNA fragment will form a hairpin region due to the interaction between the complementary sequences. In contrast, as shown on the left, if a ligated DNA fragment does not include the target region nucleotide sequence, the hairpin region will not form.

Referring to FIG. 6, digestion is performed on the cooled DNA fragments using a digestion mechanism such as, for example, 3' ssDNA digestion using an exonuclease or a polymerase with ssDNA exonuclease activity to remove the first adapter sequence (Common Adapter A) and the second adapter sequence (Common Adapter B) from the non-hairpinned DNA fragments that did not include the target region nucleotide sequence. On the hairpinned strands, the at first and second adapter sequences remain ligated to the strand.

The hairpinned DNA fragments are primed using a first primer sequence, such as Common Primer A, that matches the first adapter sequence, such as Common Adapter A. The primed hairpinned DNA fragments are then extended via the polymerase.

The resulting double-stranded, hairpinned DNA is subsequently denatured to separate it into separate strands and primed with a second primer sequence, such as Common Primer B. The second primer sequence matches the second adapter sequence, such as Common Adapter B.

A PCR protocol is performed on the DNA fragments including the first primer sequence and second primer sequence. The product of this PCR process is advantageously enriched with strands that include the target region nucleotide sequence. These strands may be cleaned up for subsequent analysis.

The steps that are bracketed in FIG. 6 may be performed as described above or may be combined in a single reaction if the polymerase used has exonuclease activity.

If desired, the products of multiple PCR protocols following these steps may be pooled.

If desired, the amplified DNA fragments may be selected by size according to a DNA size selection method, such as Pippin HT.

In some examples of the methods time and cost savings can be made by combining exonuclease digestion, priming, and polymerase extension steps by using a polymerase with 3' exonuclease activity. In such examples, the polymerase (with 3' exonuclease activity and both the first and second primer sequences with a sufficient number of 3' Phosphorothioate bonds to discourage exonuclease digestion may be added simultaneously to the hairpinned mixture at low temperature.

The temperature is kept sufficiently low to hinder polymerase activity but sufficiently high to allow exonuclease activity. After sufficient time has elapsed to allow digestion of non-hairpinned fragments, the reaction can be warmed to a high temperature temporarily prior to primer annealing, extension and PCR cycling steps.

A hot start polymerase can be used to ensure polymerase activity does not occur until activated at high temperatures (a.k.a. hot start). The exonuclease activity of the polymerase may also be disabled during this high temperature stage. This combination of steps circumvents a cleanup that would otherwise be needed between the exonuclease digestion and polymerase extension steps and reduces handling time.

The methods advantageously uses a combination of adapter design, hairpin formation, and exonuclease or exonuclease-like digestion to enrich samples of a target region of the genome.

The methods can be performed using relatively little hands-on laboratory efforts, but still produces DNA or RNA libraries that can be sequenced.

The methods have applications in numerous areas of genotyping and DNA sequencing of humans and other organisms.

Nucleic acids employed in the compositions and methods may be any nucleic acids. For example, the nucleic acid may include a DNA molecule defining the sequence of bases adenine (A), guanine (G), thymine (T), and cytosine (C) in any combination. Nucleic acids including bases other than A, T, G, and C, may also be utilized. For example, a nucleic acid including uracil (U) may be employed. In addition, bases including, but not limited to, synthetic bases may be incorporated into the nucleic acids, such as 3-methyl-6-amino-5-(1'-β-D-2'-deoxyribofuranosyl)-pyrimidin-2-one (S), 6-amino-9[(1'-β-D-2'-deoxyribofuranosyl)-4-hydroxy-5-(hydroxymethyl)-oxolan-2-yl]-1H-purin-2-one (B), 6-amino-3-(1'-β-D-2'-deoxyribofuranosyl)-5-nitro-1H-pyridin-2-one (Z), and 2-amino-8-(1'-β-D-2'-deoxyribofurano-syl)-imidazo-[1,2a]-1,3,5-triazin-[8H]-4-one (P). Any nucleic acid may be used.

The DNA including the target region nucleotide sequence may include a double-stranded DNA (dsDNA) molecule that is subsequently converted into two single-stranded DNA (ssDNA) molecules. One or both of the single-stranded DNA (ssDNA) molecules may include the DNA target region nucleotide sequence. The DNA target region nucleotide sequence is the nucleotide sequence of the DNA molecule that is desired to be amplified.

Under appropriate conditions, RNA may alternatively be used.

The compositions and methods are not limited to the details described in connection with the example embodiments. There are numerous variations and modification of the compositions and methods that may be made without departing from the scope of what is claimed.

---

That which is claimed is:

1. A method comprising:

ligating a partially double-stranded adapter nucleotide sequence comprising (i) a common adapter sequence and (ii) a probe nucleotide sequence complementary to a target region nucleotide sequence to a target DNA sequence or target RNA sequence comprising the target region nucleotide sequence to form a ligated nucleotide sequence;

denaturing the ligated nucleotide sequence to separate the ligated nucleotide sequence into a single-stranded nucleotide sequence;

cooling the single-stranded nucleotide sequence to allow the single-stranded nucleotide sequence to form a hairpin region when the single-stranded nucleotide sequence includes the target region nucleotide sequence;

digesting the single-stranded nucleotide sequence to remove the adapter nucleotide sequence if the single-stranded nucleotide sequence does not include the target region nucleotide sequence; and amplifying the single-stranded nucleotide sequence with the formed hairpin region by hybridizing a common primer on the single-stranded nucleotide sequence with the formed hairpin region and extending the common primer.

2. The method of claim 1, wherein amplifying is achieved by a polymerase chain reaction.

3. The method of claim 1, wherein the common primer is Common Primer A.

4. The method of claim 1, wherein the common adapter sequence is Common Adapter A.

5. The method of claim 1, wherein amplifying includes priming the single-stranded nucleotide sequence with Common Primer A and Common Primer B.

6. The method of claim 1, wherein:

in the cooling step, the single-stranded nucleotide sequence does not form the hairpin region when the single-stranded nucleotide sequence does not include the target region nucleotide sequence; and in the digesting step, the adapter nucleotide sequence is not removed from the single-stranded nucleotide sequence when the single-stranded nucleotide sequence includes the target region nucleotide sequence because the formed hairpin region protects the adapter nucleotide sequence.

7. A method comprising:

selectively amplifying a target DNA sequence or target RNA sequence containing a pre-determined target region nucleotide sequence therein by:

(a) ligating a partially double-stranded adapter nucleotide sequence comprising (i) a common adapter sequence and (ii) a probe nucleotide sequence complementary to the target region nucleotide sequence to the target DNA sequence or RNA sequence to form a ligated nucleotide sequence;

(b) denaturing the ligated nucleotide sequence to separate the ligated nucleotide sequence into a single-stranded nucleotide sequence;

(c) cooling the single-stranded nucleotide sequence from (b), wherein a hairpin region forms therein when the target region nucleotide sequence is present due to the probe nucleotide sequence bonding to the target region nucleotide sequence, and the hairpin region does not form therein when the target region nucleotide sequence is absent;

(d) digesting the single-stranded nucleotide sequence from (c), wherein the adapter nucleotide sequence is removed therefrom when the target region nucleotide sequence is absent, and the adapter nucleotide sequence is not removed therefrom when the hairpin region formed in (c); and (e) amplifying the single-stranded nucleotide sequence from (d) for which the hairpin region formed in (b) and the adapter nucleotide sequence was not removed in (d) by hybridizing a common primer thereon and extending the common primer.

* * * * *

SEQUENCE LISTING

```
Sequence total quantity: 4
SEQ ID NO: 1              moltype = DNA   length = 32
FEATURE                   Location/Qualifiers
misc_feature              1..32
                          note = Synthetic nucleotide sequence
source                    1..32
                          mol_type = other DNA
                          organism = synthetic construct
SEQUENCE: 1
gatcggaaga gcgtcgtgta gggaaagagt gt                              32

SEQ ID NO: 2              moltype = DNA   length = 34
FEATURE                   Location/Qualifiers
misc_feature              1..34
                          note = Synthetic nucleotide sequence
source                    1..34
                          mol_type = other DNA
                          organism = synthetic construct
SEQUENCE: 2
```

-continued

```
gtgactggag ttcagacgtg tgctcttccg atct                              34

SEQ ID NO: 3           moltype = DNA   length = 63
FEATURE                Location/Qualifiers
misc_feature           1..63
                       note = Synthetic nucleotide
misc_difference        30..37
                       note = n is a, c, g, or t
source                 1..63
                       mol_type = other DNA
                       organism = synthetic construct
SEQUENCE: 3
aatgatacgg cgaccaccga gatctacacn nnnnnnnaca ctctttccct acacgacgct   60
ctt                                                                63

SEQ ID NO: 4           moltype = DNA   length = 53
FEATURE                Location/Qualifiers
misc_feature           1..53
                       note = Synthetic nucleotide
misc_difference        25..32
                       note = n is a, c, g, or t
source                 1..53
                       mol_type = other DNA
                       organism = synthetic construct
SEQUENCE: 4
caagcagaag acggcatacg agatnnnnnn nngtgactgg agttcagacg tgt           53
```